(12) United States Patent
Massengill

(10) Patent No.: US 6,464,694 B1
(45) Date of Patent: *Oct. 15, 2002

(54) LASER-ASSISTED LIPOSUCTION METHOD AND APPARATUS

(75) Inventor: R. Kemp Massengill, Leucadia, CA (US)

(73) Assignee: Sonique Surgical Systems, Inc., Escondido, CA (US)

( * ) Notice: Subject to any disclaimer, the term of this patent is extended or adjusted under 35 U.S.C. 154(b) by 67 days.

This patent is subject to a terminal disclaimer.

(21) Appl. No.: 09/624,886

(22) Filed: Jul. 24, 2000

Related U.S. Application Data

(63) Continuation-in-part of application No. 09/182,535, filed on Oct. 29, 1998, now Pat. No. 6,106,516.

(51) Int. Cl.[7] .................................................. A61B 18/18
(52) U.S. Cl. .................................. 606/15; 606/2; 607/89
(58) Field of Search .......................... 606/2, 7, 9, 10, 606/11, 12–16, 17; 607/89; 604/20

(56) References Cited

U.S. PATENT DOCUMENTS

| 4,646,737 A | 3/1987 | Hussein et al. |
| 4,681,104 A | 7/1987 | Edelman |
| 4,686,979 A | 8/1987 | Gruen et al. |
| 4,694,828 A | 9/1987 | Eichenbaum |
| 4,744,360 A | 5/1988 | Bath |
| 4,985,027 A | 1/1991 | Dressel |
| 5,102,410 A | 4/1992 | Dressel |
| 5,129,896 A | 7/1992 | Hassen |
| 5,324,282 A | 6/1994 | Dodick |
| 5,370,608 A | 12/1994 | Sahota et al. |
| 5,741,247 A | 4/1998 | Rizoiu |
| 5,785,521 A | 7/1998 | Rizoiu |
| 5,817,050 A | 10/1998 | Klein |
| 5,947,988 A | 9/1999 | Smith |
| 5,957,914 A | 9/1999 | Cook et al. |
| 6,139,571 A | * 10/2000 | Fuller et al. ................ 604/113 |
| 6,203,540 B1 | * 3/2001 | Weber ........................ 604/22 |
| 6,206,873 B1 | * 3/2001 | Paolini et al. ............... 606/15 |
| 6,254,597 B1 | * 7/2001 | Rizoiu et al. ................ 604/35 |

OTHER PUBLICATIONS

Alzner, Egon; *Dodict Laser Phacolysis–Thermal Effects*; nine pages; place and date of publication unknown.

Brazzo, Brian G.; Erbium Laser Skin Resurfacing Gives Less Thermal Effect; Oct. 15, 1997; Ocular Surgery News; pp. 116, 117.

Kanellopoulos, A., et al.; Dodick Photolysis for Cataract Surgery Early Experience with the Q–switched Neodymium: YAG Laser in 100 Consecutive Patients; Nov. 11, 1998; Ophthalmalogy; vol. 106, No. 11, Nov. 1999; pp. 2198–2202.

Klein, Jeffrey; Recipes for Tumescent Local Anesthetic Solutions in 0.9% NaCl; Lecture material update; Oct., 1998; 2 pages.

Singer, H.; Laser Phaco Makers Aiming for Safety Improvements, Shorter Learning Curve; Aug. 15, 1997; Ocular Surgery News; 4 pages.

* cited by examiner

*Primary Examiner*—Roy D. Gibson
(74) *Attorney, Agent, or Firm*—Gerald W. Spinks

(57) ABSTRACT

A liposuction cannula having a source of aqueous solution, a laser source, and a suction source. Aqueous solution is released into an active area within the cannula, and laser energy is directed onto the aqueous solution within the active area to energize the water molecules. The energized water molecules escape from the active area into the surrounding fatty tissue to break down the fatty tissue and release liquid fatty material, which is removed by aspiration via the cannula.

17 Claims, 7 Drawing Sheets

LASER-ASSISTED LIPOSUCTION METHOD AND APPARATUS

CROSS REFERENCE TO RELATED APPLICATIONS

This application is a continuation-in-part of U.S. patent application Ser. No. 09/182,535, filed on Oct. 29, 1998, now U.S. Pat. No. 6,106,516 and entitled "Laser-Assisted Liposuction Method and Apparatus."

STATEMENT REGARDING FEDERALLY SPONSORED RESEARCH OR DEVELOPMENT

Not Applicable

BACKGROUND OF THE INVENTION

1. Field of the Invention

This invention is in the field of liposuction surgery, a plastic cosmetic procedure in which fat cells are removed permanently from the body.

2. Background Information

Conventional liposuction, which features suction as the only active modality for removing unwanted fat cells, is a procedure fraught with complications, including excessive postoperative pain and the potential for major hemorrhagic complications. Several deaths have been reported because of the crudity of conventional liposuction. The mechanism in conventional liposuction is that suction tears the fat cells from their attachments. Unfortunately, suction also tears nerves and blood vessels.

Early attempts to use the laser as the operational modality for liposuction surgery met with failure, as the laser was too powerful an energy source. Heat from the laser, which was applied directly to the fat, would, in fact, melt and liquify fatty tissues, but, at the same time, this strong energy source would also damage nerves and blood vessels. In other words, the laser as employed for liposuction in the late 1980s had, in essence, a quite similar complication rate to that of conventional suction-only liposuction. Laser liposuction fell into disfavor and was abandoned as a failure.

An advance in the use of lasers for medical procedures occurred during experimentation with "laser phacolysis", a method for removing cataracts through a very small incision. It was noted that, although heat was produced by the laser, the tip of the phacolysis cataract instrument remained essentially cool. The proposed mechanism of action of the laser used there was that the laser light was focused on a metal target inside the tip. Optical breakdown occurs, leading to a shock wave. It is this shockwave which causes disruption of the cataract. In other words, the laser works indirectly as a facilitator, allowing the shockwave resulting from optical breakdown to do the actual work of breaking the quite-hard cataract into small pieces, which can then be aspirated.

BRIEF SUMMARY OF THE INVENTION

In the present invention, laser energy is emitted into an "active area" located within the distal end of the cannula. Simultaneously, one or more jetstreams of water or aqueous solution are emitted into this same active area.

The laser bombards the water molecules supplied by the jetstream, and, secondary to this laser energy bombardment and the subsequent impartation of laser energy from the laser to the water molecules, the water molecules become extremely agitated. These "hyperkinetized" water molecules escape from the active area within the distal cannula tip through holes or ports into the substrate fatty tissue. The violently moving water molecules disrupt the adipocyte cell walls, releasing the liquidous material within the cells. This liquified fat is then aspirated by the cannula through one or more suction ports of the cannula, which is attached proximally to an outflow tube connected to a suction pump apparatus. The aspiration suction ports are preferably located on the lateral aspect of the cannula proximal to the active area, but, alternatively, a suction port can also be employed at the extreme distal end of the cannula via a tube traversing the active area and connecting to the internal hollow aspect of the cannula proximal to the active area.

The process may be observed via an endoscope attached separately to the external surface wall of the cannula. This feature is primarily useful for eyelid, face, and neck procedures.

The novel features of this invention, as well as the invention itself, will be best understood from the attached drawings, taken along with the following description, in which similar reference characters refer to similar parts, and in which:

DETAILED DESCRIPTION OF THE INVENTION

There are two mechanisms of action which may be brought into play in the present invention as follows:

(A) a "water-blasting" mechanical effect of the water molecules against the adipocyte walls, similar to "sandblasting", but using highly energized water molecules instead of sand; or, (B) a transfer of heat from the highly-energized water molecules to the adipocyte cells walls, or a combination of both (A) and (B).

The intense heat transferred by the laser and absorbed by the water molecules is very transient in duration, however. This is related, it is believed, to the very small mass of the individual water molecules, such that a significant temperature rise in the substrate fatty tissues does not occur. Thus, the burning noted with prior attempts to perform laser liposuction surgery is absent with the presently-disclosed invention. In other words, an intense heat source—the laser—is essentially "cool" in the present invention, in that temperature elevation does not occur to any significant degree in the fatty tissues. It must be kept in mind that in the present invention, application of the laser energy to the fatty tissues is indirect, in that it is not the laser which is performing the surgery, but rather the highly-energized water molecules.

It is commonly recognized that cell death occurs when tissues are heated for any length of time beyond 43 degrees C. Because temperature elevation within the substrate fatty tissue is kept below 43 degrees, damage to nerves and blood vessels during practice of the present invention is minimized.

The present invention operates differently from other medical "cool lasers", such as dental lasers, in that the jet-stream of water or aqueous solution is directed into an active area within the cannula, rather than being directed externally from the cannula into, or onto, the surrounding tissue, such as with dental procedures or skin resurfacing procedures.

Figure 1:
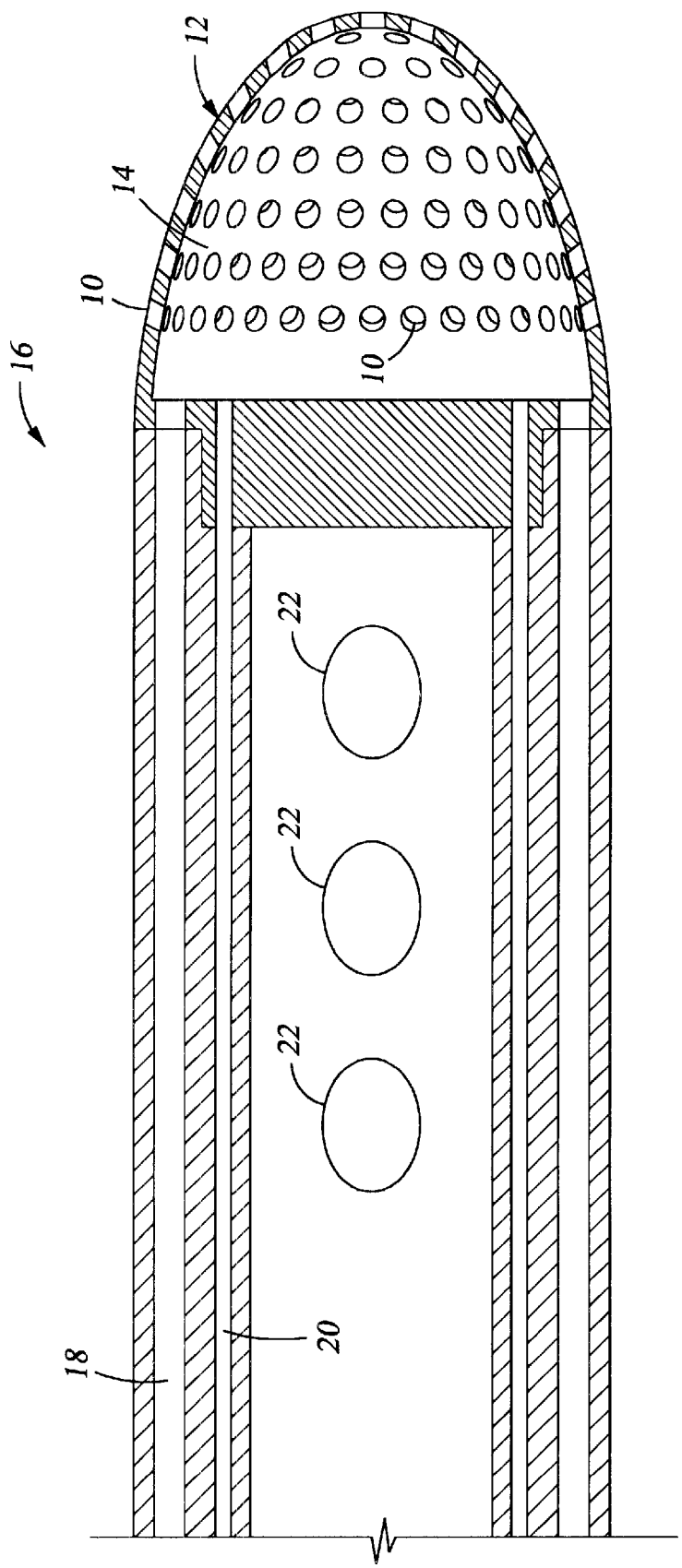
FIG. 1 is a section view of one embodiment of the present invention, showing a walled enclosure around the active area and lateral suction ports.
Figure 8:
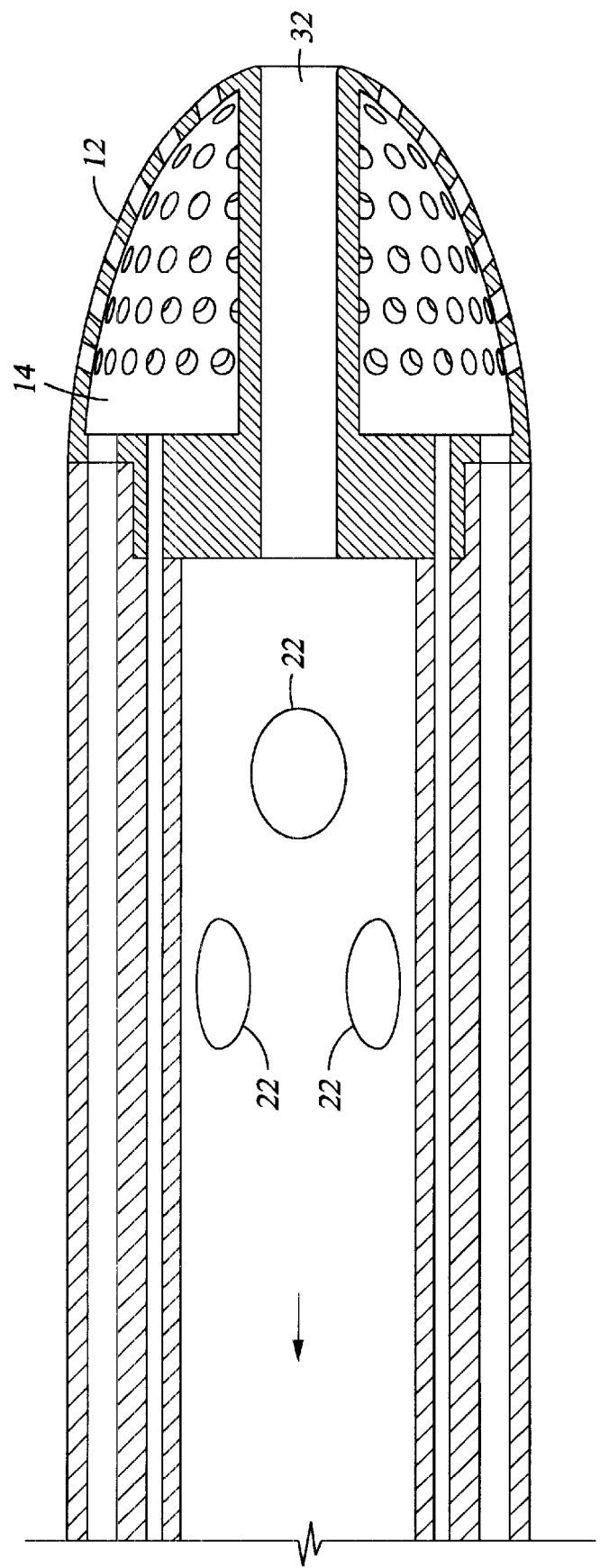
FIG. 8 is a section of a third embodiment of the present invention, showing a distal suction port and lateral suction ports.

In one embodiment, shown in FIG. 1, a plurality of ports, openings, or holes 10 are formed in a substantially rigid walled enclosure 12 around the "active area" 14 of the cannula 16, allowing the highly-energized water molecules to leave the active area 14 within the cannula 16, thus reaching the substrate fatty tissue. One or more fluid channels 18 conduct water or aqueous solution to the active area 14, and one or more optical fibers 20 conduct laser energy to the active area 14. One or more lateral suction ports 22 can be provided in the wall of the cannula 16, for aspirating liquid fatty material. FIG. 8 illustrates that a suction port 32 can also be employed at the extreme distal end of the cannula 16 via a tube traversing the active area 14 and connecting to the internal hollow aspect of the cannula 16 proximal to the active area 14.

Figure 2:
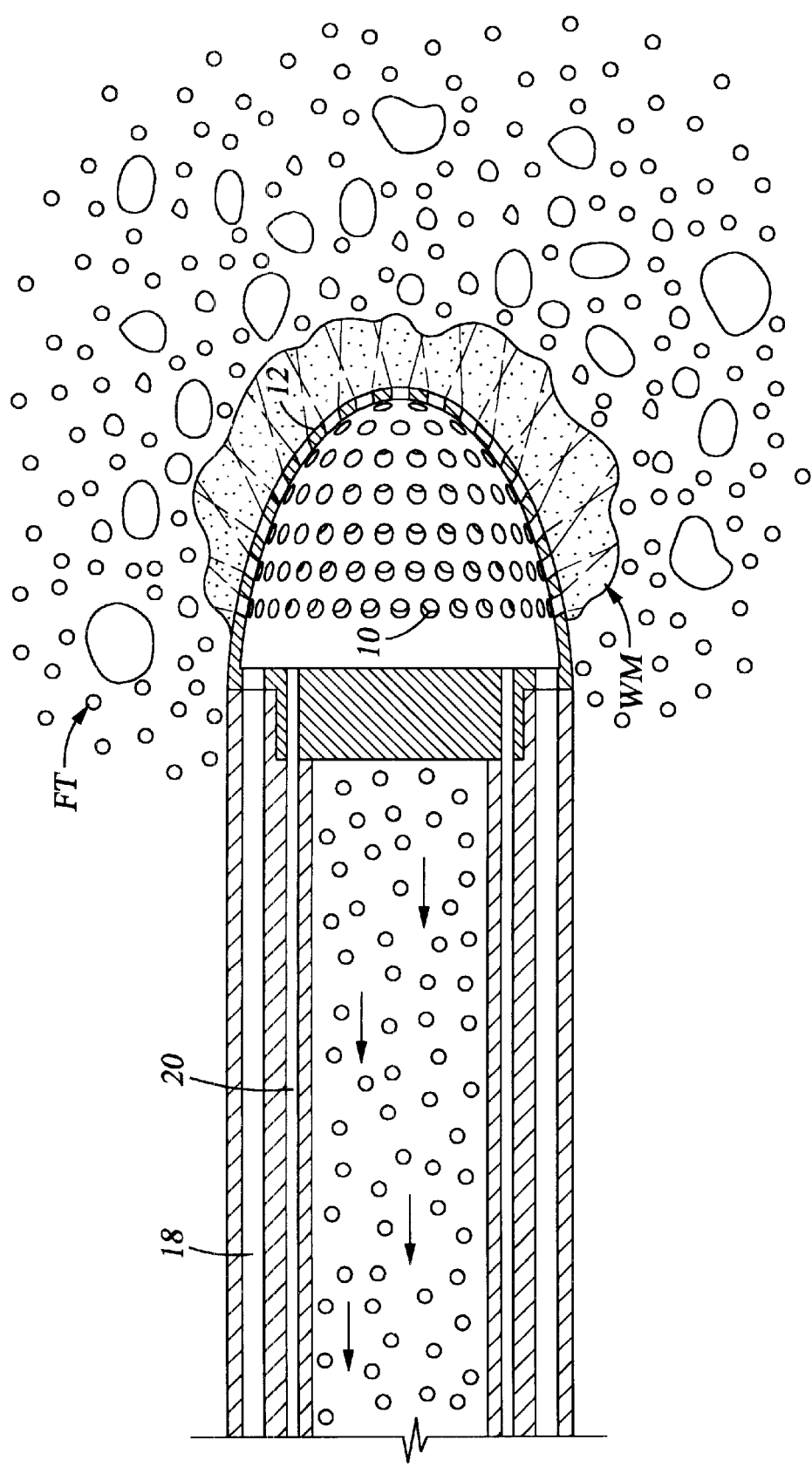
FIG. 2 is a schematic view of the interaction of the present invention with surrounding fatty tissues.

FIG. 2 illustrates how the energized water molecules WM exit the active area 14 via the ports 10 in the walled enclosure 12, to break down the fatty tissue FT and liquefy the fatty material.

Figure 3:
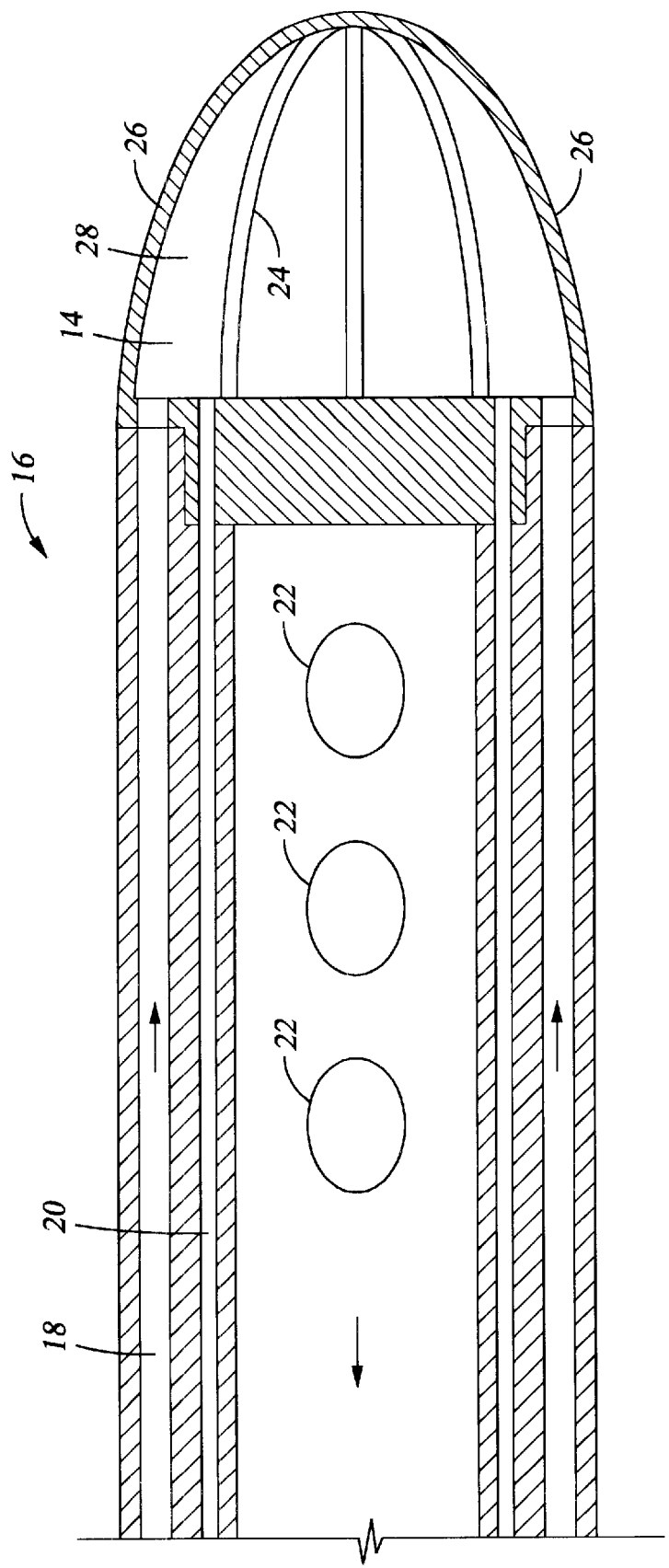
FIG. 3 is a section view of a second embodiment of the present invention, showing a scaffold type enclosure around the active area and lateral suction ports.

In another embodiment, shown in FIG. 3, a ribbed "scaffolding-style" tip 24 on the distal end of the cannula 16, in essence, is another embodiment of the substantially rigid enclosure which creates an "intracannular" space which constitutes the enclosed active area 14, which is separated physically from the fatty tissue itself by the scaffolding ribs 26, as they glide through the fatty tissue. The energized water molecules exit jets in the cannula 16 between the scaffolding ribs 26 in this embodiment. Both embodiments, that is, the ported embodiment and the ribbed embodiment have practical applications.

The preferred embodiment, in either case, has a "bullet-shaped" distal tip 12, 24, as this reduces the friction required to part and to separate the fatty tissue as the cannula 16 glides through the tissue in a back and forth fashion. A little side movement is permitted on each forward thrust, as the surgeon finds a new area to treat. Surgeon fatigue is kept to a minimum with such a bullet-shaped distal tip. In addition, less tissue trauma is attendant with the use of a bullet-tip. The bullet shaped tip can be employed either in the ported embodiment or the scaffolding embodiment. A flatter tip, although not the preferred embodiment, is not intended to be excluded from this invention, however.

Figure 7:
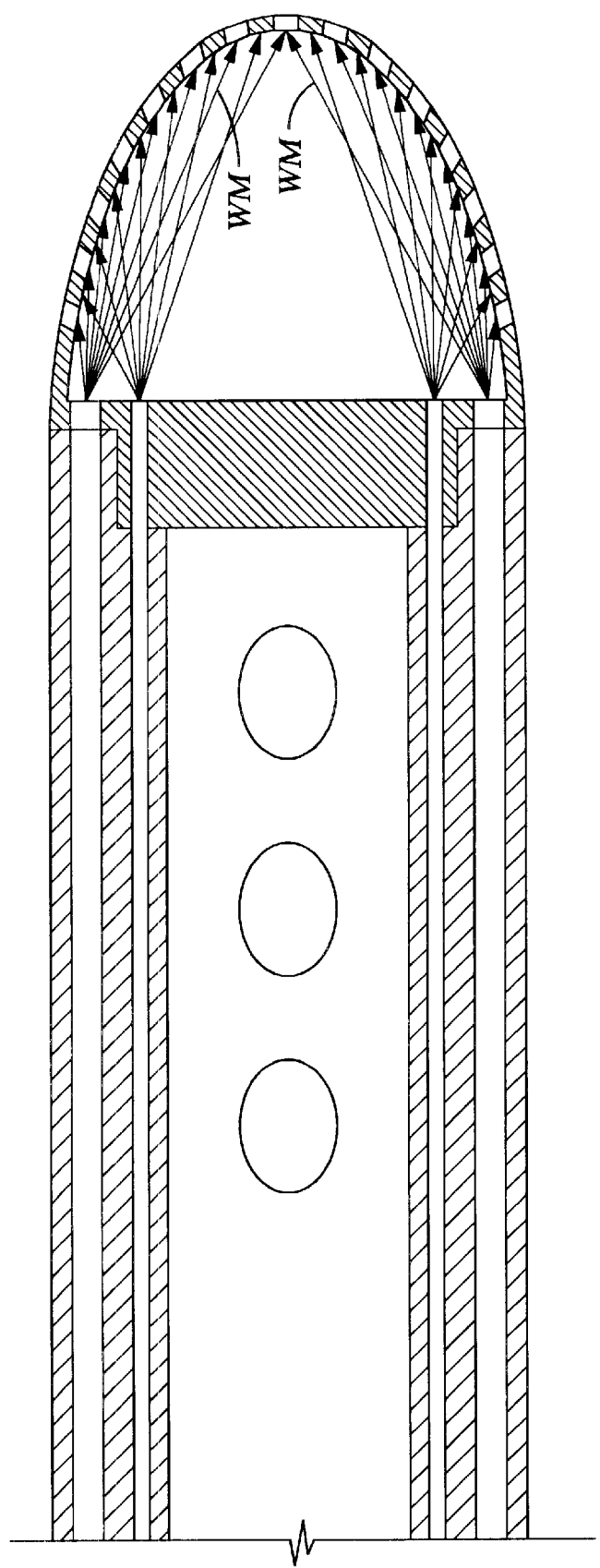
FIG. 7 is a schematic view of the different angles at which the fluid may be directed into the active area.

The laser optical fibers 20 and the fluid jetstream channels 18 course through the outer walls of the hollow cannula 16 to the proximal aspect of the active area 14, thus allowing laser emissions and fluid jetstream discharge into the active area 14. A plurality of such laser fibers 20 and fluid jetstream channels 18 is envisioned in the preferred embodiment. However, for extremely delicate operations, such as to remove fatty tissue from the lower eyelids, a single jetstream and a single laser optical fiber can be utilized. These laser fibers 20 and fluid channels 18 can be directed at different angles into the active area 14, as shown in FIG. 7, so that the water molecules can be hyperkinetized in a specific part of the active area 14, or throughout, the active area 14.

Figure 4A:
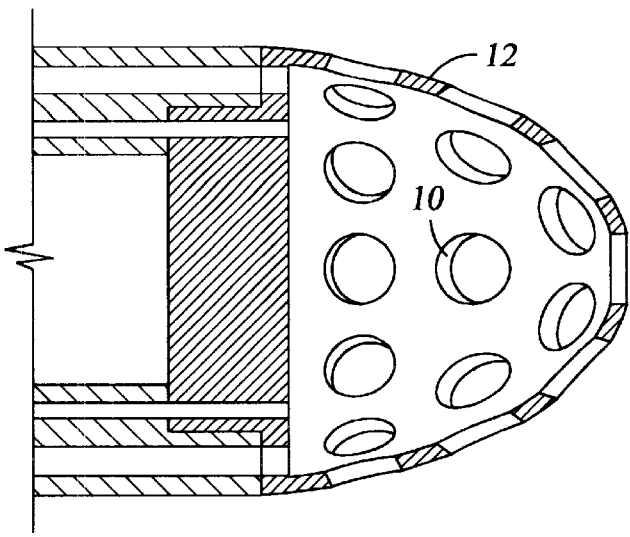
FIGS. 4A, 4B, and 4C are schematics showing three different embodiments of the openings in the walled enclosure around the active area.
Figure 4B:
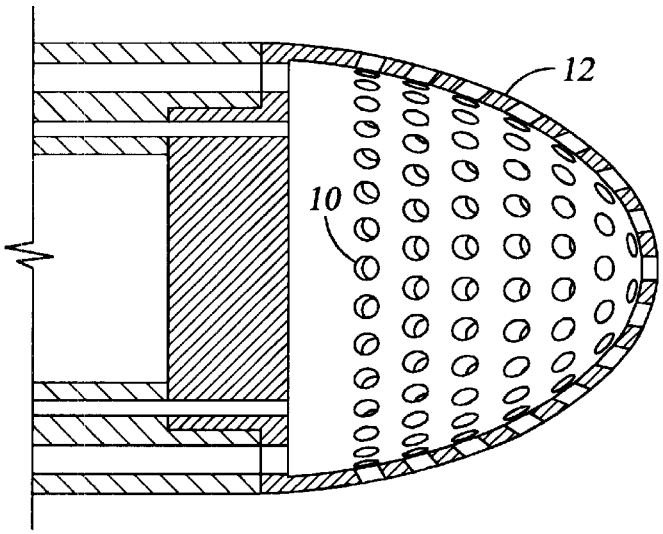
Figure 4C:
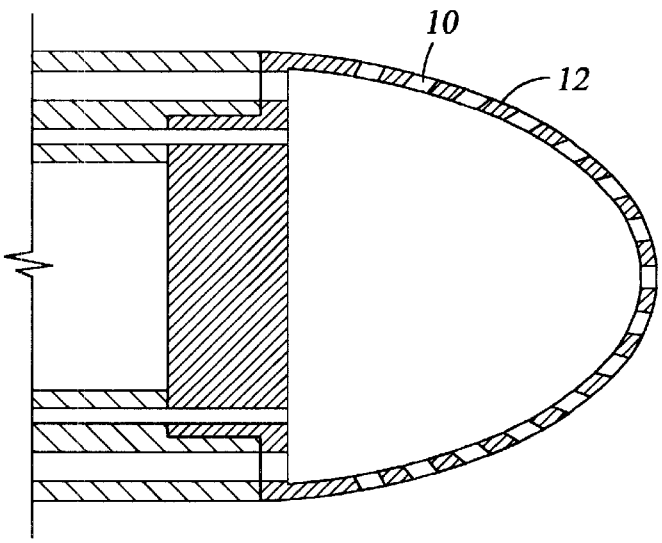

In the ported embodiment, the ports 10 in the distal tip enclosure 12 can be very small, such as 0.25 mm. in diameter, or quite large, such as 2.5 to 3.0 mm. in diameter, or even larger, as illustrated in FIGS. 4A and 4B. Further, the ports 10 can be positioned throughout the enclosure wall 12, or limited to the lateral aspect thereof, as in FIG. 4C.

Figure 5:
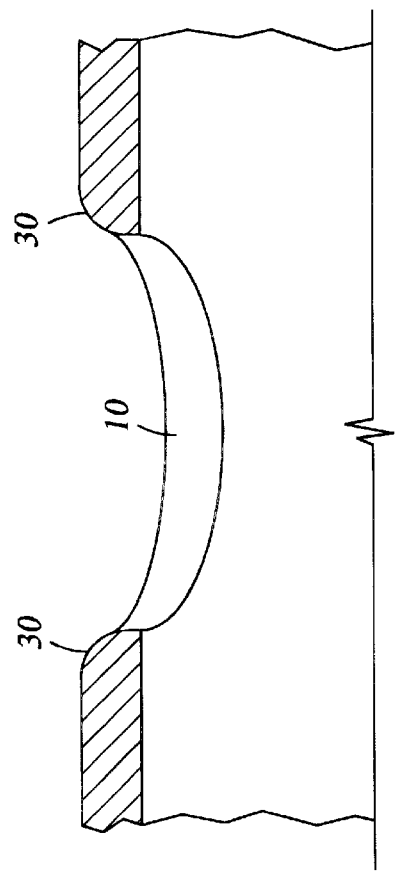
FIG. 5 is a partial section of the rigid enclosure, showing the rounded edges which can be used on the openings in the enclosure around the active area.

The edges 30 of the ports 10, and the edges of the scaffolding ribs 26, should be specially treated to be rounded and smoothed, as shown in FIG. 5, since any sharp edge of the hole tends to function in a knife-like fashion, which is undesirable. In addition, the walls of the cannula 16 immediately adjacent to the port 10 can be built up circumferentially to minimize even further any potential cutting action attributable to the ports 10 themselves.

Figure 6:
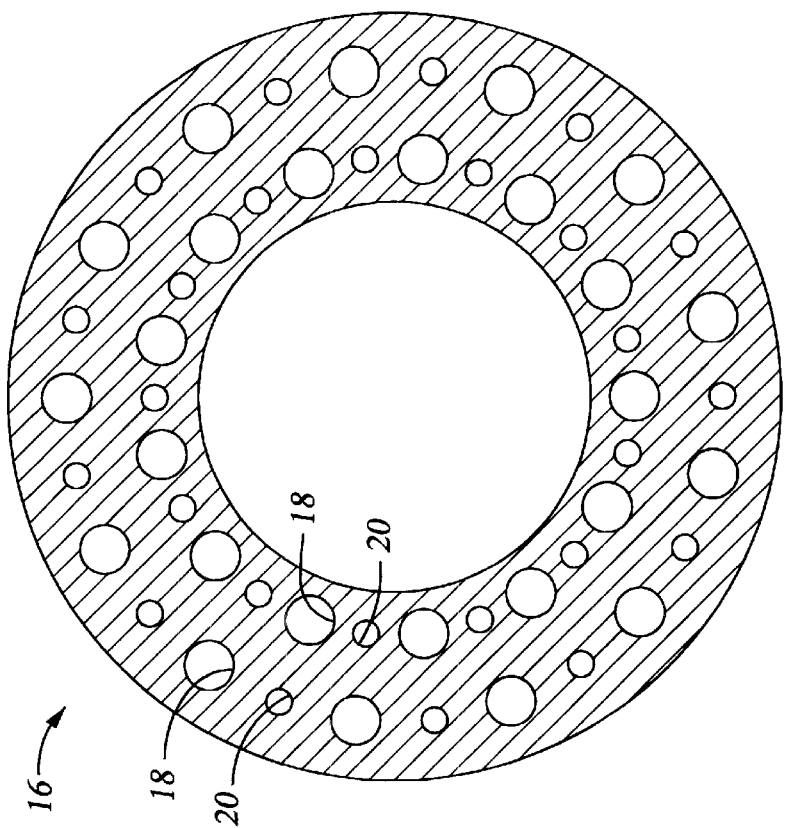
FIG. 6 is a transverse section of the cannula, showing one arrangement of the fluid channels and optical fibers.

The laser fibers 20 and fluid jetstream channels 18 may be in a single row, or two, three, or more rows, traversing within the walls of the cannula 16, as shown in FIG. 6. The laser fibers 20 or fluid jetstream channels 18 may also traverse through a longitudinal tube extending up the axis of the cannula 16, or off center but parallel to the axis, if desired. Nevertheless, both the laser energy and at least one fluid jetstream must be supplied into the active area 14 within the cannula 16, with the laser beam not exiting the cannula 16, as this allows for the hyperkinetization effect of the laser energy upon the water molecules in a safe, internal environment, namely, the active area 14. Supplying the jetstream and the laser directly into or onto the tissue external to the cannula 16 would be quite dangerous, as the laser would then be in a physical position to operate directly upon the substrate fatty tissue. The purpose of the present invention is to prevent any possibility of the direct action of the laser on the surrounding tissue.

The cool lasers presently used in oral or dental treatments, and in skin resurfacing, would not be suitable for the removal of fatty tissue. As opposed to a very hard tissue, such as dental tissue, or a soft, but yet relatively firm tissue, such as skin, fatty tissue is composed of uniquely fragile fat cells. In fact, fat cells are among the most fragile cells in the entire body.

The present invention allows for preferentially treating fat cells, while sparing nearby blood vessels and nerve cells. In this invention, the very fragile fat cell walls are disrupted, thus releasing liquidous fatty material to be aspirated, while the blood vessel walls, which are sturdier in construction than those of fat cells, are generally spared. It is fat cells which are preferentially attacked by the highly energized, hyperkinetized water molecules. For this reason, bleeding from blood vessel damage is minimized. Likewise, nerve damage tends to be minimized, in that the larger pain nerves tend to be more robust than the extremely delicate fat cells.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

I claim:

1. An apparatus for removal of fatty tissue, comprising:

a hollow cannula;

a substantially rigid enclosure on said cannula, said enclosure being shaped to enclose an active area within said cannula, and protect said active area from intrusion by surrounding tissues;

a fluid source on said cannula, said fluid source being disposed to release aqueous solution into said active area enclosed within said cannula;

a laser source on said cannula, said laser source being disposed to impinge laser energy on said aqueous solution from said fluid source in said active area enclosed within said cannula, to energize water molecules in said aqueous solution, said laser source being arranged relative to said fluid source and said enclosure so as to prevent escape of any laser energy from said enclosure prior to impingement of said laser energy upon said water molecules;

an opening in said enclosure, said opening being positioned to allow said energized water molecules to escape from said enclosure to contact and break down surrounding fatty tissues; and a suction port on said cannula for aspirating liquid material resulting from breakdown of surrounding fatty tissues.

2. An apparatus for removal of fatty tissue, as recited in claim 1, wherein said enclosure comprises a portion of a wall of said cannula, with said active area being enclosed within said portion of said wall.

3. An apparatus for removal of fatty tissue, as recited in claim 1, wherein said enclosure comprises a plurality of substantially rigid ribs attached to said cannula, with said active area being substantially surrounded by said ribs.

4. An apparatus for removal of fatty tissue, as recited in claim 1, wherein said fluid source comprises at least one fluid jet positioned to spray aqueous solution into said active area.

5. An apparatus for removal of fatty tissue, as recited in claim 1, wherein said laser source comprises at least one optical fiber positioned to direct at least one laser beam on said aqueous solution within said active area.

6. An apparatus for removal of fatty tissue, as recited in claim 1, wherein said aqueous solution comprises a saline solution.

7. An apparatus for removal of fatty tissue, as recited in claim 6, wherein said saline solution comprises a balanced salt solution.

8. An apparatus for removal of fatty tissue, as recited in claim 1, wherein said aqueous solution comprises Ringer's lactate.

9. An apparatus for removal of fatty tissue, as recited in claim 1, wherein said aqueous solution comprises a dextrose solution.

10. An apparatus for removal of fatty tissue, as recited in claim 6, wherein said aqueous solution includes lidocaine, epinephrine, and sodium bicarbonate.

11. A method for removal of fatty tissue, said method comprising:

providing a hollow cannula having a substantially rigid enclosure, a source of aqueous solution, a laser source, and a suction port;

releasing aqueous solution from said source into an active area enclosed within said rigid enclosure within said cannula;

impinging laser energy from said laser source onto water molecules in said aqueous solution in said active area enclosed within said cannula, to energize said water molecules, without allowing escape of any laser energy from said enclosure prior to impingement of said laser energy upon said water molecules;

allowing said energized water molecules to escape through openings in said enclosure to contact and break down surrounding fatty tissues; and aspirating liquid material resulting from breakdown of surrounding fatty tissues, via said suction port.

12. A method for removal of fatty tissue, as recited in claim 11, said method further comprising releasing said aqueous solution from a plurality of said sources into said active area.

13. A method for removal of fatty tissue, as recited in claim 11, said method further comprising releasing a saline solution from a plurality of said sources into said active area.

14. A method for removal of fatty tissue, as recited in claim 11, said method further comprising releasing a balanced salt solution from a plurality of said sources into said active area.

15. A method for removal of fatty tissue, as recited in claim 11, said method further comprising releasing Ringer's lactate from a plurality of said sources into said active area.

16. A method for removal of fatty tissue, as recited in claim 11, said method further comprising releasing a dextrose solution from a plurality of said sources into said active area.

17. A method for removal of fatty tissue, as recited in claim 11, said method further comprising releasing a solution including lidocaine, epinephrine, and sodium bicarbonate from a plurality of said sources into said active area.

* * * * *